(12) United States Patent
Om et al.

(10) Patent No.: US 8,143,435 B2
(45) Date of Patent: Mar. 27, 2012

(54) ONE POT PROCESS FOR THE PREPARATION OF CANDESARTAN

(75) Inventors: Dutt Tyagi Om, Hyderabad (IN); Nageswara Rao Karusala, Hyderabad (IN); Uma Sankara Sastry Tummalapalli, Hyderabad (IN); Mohan Bandari, Hyderabad (IN); Seeta Ramanjaneyulu Gorantla, Hyderabad (IN)

(73) Assignee: Mylan Laboratories Ltd., Hyderabad (IN)

( * ) Notice: Subject to any disclaimer, the term of this patent is extended or adjusted under 35 U.S.C. 154(b) by 0 days.

(21) Appl. No.: 12/445,105

(22) PCT Filed: Oct. 9, 2007

(86) PCT No.: PCT/IN2007/000469
§ 371 (c)(1),
(2), (4) Date: Jul. 13, 2010

(87) PCT Pub. No.: WO2008/044244
PCT Pub. Date: Apr. 17, 2008

(65) Prior Publication Data
US 2011/0034701 A1    Feb. 10, 2011

(30) Foreign Application Priority Data

Oct. 10, 2006  (IN) .......................... 1869/CHE/2006

(51) Int. Cl.
*C07C 255/00* (2006.01)

(52) U.S. Cl. ..................................................... 558/414
(58) Field of Classification Search .................... 558/414
See application file for complete search history.

(56) References Cited

U.S. PATENT DOCUMENTS 5,196,444 A * 3/1993 Naka et al. .................... 514/381
6,177,587 B1 * 1/2001 Hashimoto et al. ........... 558/414

FOREIGN PATENT DOCUMENTS

WO    WO 2006/015134    *    2/2006

* cited by examiner

*Primary Examiner* — Susannah Chung
(74) *Attorney, Agent, or Firm* — Ladas + Parry LLP

(57) ABSTRACT

Present invention is to provide one pot synthesis of candesartan without isolating the ester intermediate.

7 Claims, No Drawings

ONE POT PROCESS FOR THE PREPARATION OF CANDESARTAN

FIELD OF THE INVENTION

This invention, in general, relates to a one pot process for preparing candesartan. More specifically, but without restriction to the particular embodiment herein after described in accordance with the best mode of practice, the present invention provides a process for the preparation of candesartan without isolating the ester intermediate

BACKGROUND OF THE INVENTION

Candesartan is a potent, long lasting, selective $AT_1$ subtype angiotensin II receptor antagonist. The chemical name for candesartan is: 2-ethoxy-1-[[2'-(1H-tetrazol-5-yl) biphenyl-4-yl]methyl]-1H-benzimidazole-7-carboxyllic acid. Candesartan is angiotensin receptor blocker and blocks the ability of the chemical angiotensin II to raise the blood pressure by constricting or squeezing arteries and veins. This leads to a reduction in blood pressure. The mechanism is Angiotensin II is formed from Angiotensin I by the catalytic reaction of ACE kininase II. Angiotensin II effects stimulation of synthesis and release of aldosterone, cardiac stimulation, vasoconstriction and renal reabsorption of sodium. Candesartan blocks vasoconstrictor and aldosterone secreting effects of angiotensin II by selectively blocking the binding of angiotensin II to AT1 receptor in many tissues such as vascular smooth muscle and adrenal gland. By inhibiting the binding, candesartan disrupts the vasoconstriction mediated by AT1 receptors and thus helps patients with hypertension. In addition, by reducing the pressure against which the heart must pump blood, candesartan reduces the work of the heart and is useful in patients with heart failure.

U.S. Pat. No. 5,196,444 discloses the preparation of candesartan in 2 steps. First step is the formation of candesartan ethylester prepared by reacting cyano compound with trimethyltinazide in toluene for 4 days. The residue is separated and to it added methanol and conc. HCl. The mixture is stirred for 30 min and pH is adjusted to 3-4 with 1N NaOH. After removal of the solvent, the residue is partitioned between chloroform-water. The organic solvent is removed and the syrupy product is chromatographed. Yield is 45%

In the second step candesartan ethylester is added to 1N NaOH in ethanol and solution is stirred for 1 hr at 80° C. The reaction mass is concentrated and extracted with water and ethylacetate. The aqueous layer pH is adjusted to 3-4 with 1N HCl to give the candesartan crystals.

U.S. Pat. No. 5,703,110 describes the two step process which is a divisional of U.S. Pat. No. 5,196,444 claims candesartan, a pharmaceutically acceptable salt there of, pharmaceutical compositions and method for antagonizing angiotensin II in a mammal by administering a therapeutically effective amount of candesartan or a pharmaceutically acceptable salt thereof.

U.S. Pat. No. 6,177,587 describes the preparation of candesartan. In the first step candesartan methyl ester is prepared by reacting cyano intermediate with trioctyltinazide in toluene for 40 hours. The residue is separated and ethanol and sodium nitrite solution are added to it and the pH is adjusted to 4.5-5.5 with conc. HCl. To this solution ethyl acetate is added and the pH is adjusted to 0.5-1.5 with conc. HCl. To the solution hexane is added and again pH is adjusted to 3.5±0.5 with 4% sodium hydroxide solution. The solution is cooled to 10° C. or less and filtered to get methyl ester of candesartan.

In the second step candesartan methyl ester is added to NaOH solution and is stirred for 1-2 hr at 68-72° C. The solution is cooled and washed twice with dichloromethane and once with toluene. To the aqueous solution is added methanol and the solution pH is adjusted to 7.9±0.5 with conc. HCl. The solution is stirred at 25±5° C. for one hr which is added to water and the pH is adjusted to 3.5±0.3 with conc. HCl. The reaction mixture is diluted with water and cooled to 10° C. or less and the product candesartan formed is washed with acetone and dried.

WO 2005/051929 discloses a process where cyano intermediate is taken in toluene and to it added tributyltin chloride, sodium azide and tetrabutylammonium bromide. The resultant mass is slowly heated to 110° C. and maintained for 24 hrs at 110-115° C. After completion of the reaction, reaction mass is cooled to 15° C. and added methanol and water followed by acetic acid. Resultant mixture is stirred at 25-20° C. for 1 hr and once the product Candesartan methyl ester is separated added toluene and filtered the mass.

To this product added methanol, sodium hydroxide solution and heated to reflux for 1 hr. After completion of reaction methanol is completely removed and to the residue ethylacetate and water is added at room temperature. Stirred the mixture for 1 hr and allowed to settle at 10-15° C. The precipitate is filtered and washed twice with water to get candesartan.

The present invention is to provide one pot synthesis of candesartan without isolating the ester intermediate. Industrial advantage of the process is distillation of the reaction mass having azides to remove the candesartan ester is bypassed and the hydrolysis step is carried out insitu to get the final product candesartan.

SUMMARY OF THE INVENTION

In accordance with the principal aspect of the present invention, there is provided a novel one pot process for the preparation of candesartan to improve upon limitations in the prior art.

In accordance with another aspect of the present invention, there is provided a process for the preparation of candesartan comprising by reacting cyanobiphenyl benzimidazole (CBBI) (III) with trialkyltin or triaryltin azide in an organic solvent gives candesartan ethylester (II) which upon hydrolysis with an alkali followed by treatment with an acid yields candesartan (I).

The present invention is represented by the following scheme.

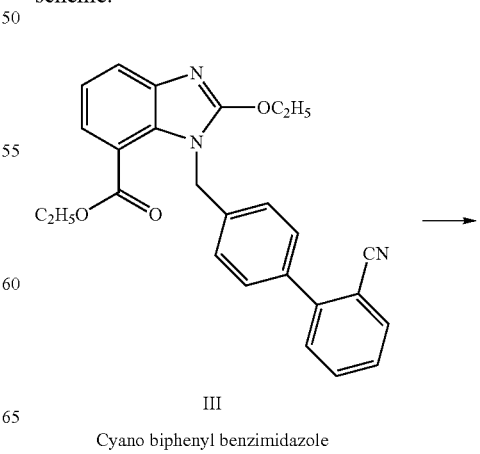

III
Cyano biphenyl benzimidazole

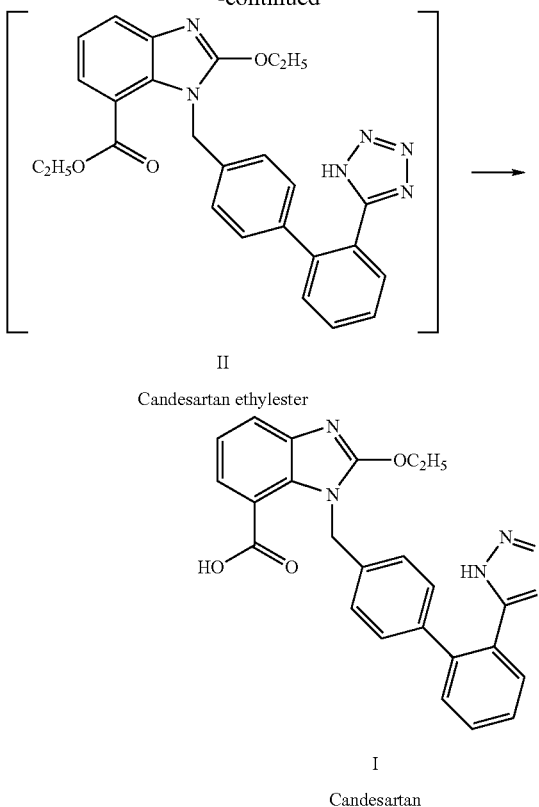

II
Candesartan ethylester

I
Candesartan

DETAILED DESCRIPTION OF THE INVENTION

The present invention describes a convenient, industrially feasible and efficient one pot process for the preparation of candesartan. Thus in accordance with the present invention process for the preparation of candesartan comprises:
(a) reacting cyanobiphenyl benzimidazole (III) with trialkyltin or triaryltin azide in presence of an organic solvent to form candesartan ethylester (II); and
(b) insitu hydrolyzing candesartan ethyester (II) with an alkali followed by treatment with an acid gives candesartan (I).

The present invention describes in the first step the preparation of candesartan ethylester (II), which involves the reaction of cyanobiphenyl benzimidazole (III) with trialkyltin or triaryltin azide, examples of such azides include trimethyltin azide, tributyltin azide, triphenyltin azide but preferably tributyltin azide (prepared from the reaction of sodium azide with trialkyl or triaryltin chloride) in an organic solvent. The organic solvent used herein is selected from but not limited to o-xylene, toluene, dimethylformamide, dimethylacetamide and the like, preferably o-xylene. The reaction is carried out at a temperature range of about 100 to 150° C. preferably at reflux temperature over a period of about 20-24 hours.

Once the tetrazole product candesartan ethylester (II) is formed, it is hydrolyzed in presence of an alkali to give candesartan (I). This reaction is conducted in situ without the isolation of ester compound (II). Examples of such alkali include sodium hydroxide, potassium hydroxide etc., preferably sodium hydroxide. Addition of sodium hydroxide is carried out at a temperature range of about 20-35° C. Once addition is complete hydrolysis is carried out at a temperature range of about 50-65° C. On the completion of the reaction, aqueous and organic layers are separated. The aqueous layer is extracted with alcohols such as methanol, ethanol preferably methanol at a temperature range of 25-35° C. and adjusted the pH with acids preferably acetic acid to 4.5 to 5.5. Candesartan formed is filtered and dried at 60-70° C. till the moisture content is not more than 1.0%.

The examples mentioned below explain all the aspects of the present invention. The examples are given to illustrate the details of the invention and should not be construed to limit the scope of the present invention.

EXAMPLE 1

Preparation of Candesartan

Sodium azide (50 gm) was taken in water (160 ml) at 25-35° C. followed by the addition of tributyltinchloride (230 gm). This reaction mixture was cooled to 5-10° C. and maintained for 2 hrs followed by the addition of o-xylene (600 ml). After 10 min, the xylene layer was separated. In another flask cyanobiphenyl benzimidazole (100 gm) was taken in o-xylene (200 ml) at 25-35° C. First xylene layer was added to second flask and refluxed. On the completion of reaction, reaction mass was cooled to 25-35° C. followed by the addition of aq. sodium hydroxide solution (47 gm of NaOH in 800 ml of DM water). The temperature was raised to 55-65° C. and maintained for 3 hrs. Once the reaction was complete, separated the aqueous layer and extracted with 600 ml of methanol. Methanol extract was filtered through hy-flow bed and the filtrate pH was adjusted to 4.5 to 5.5 by slow addition of 200 ml of acetic acid. The product candesartan formed was filtered and washed with DM water followed by 200 ml of acetone. The product was dried at 60-70° C. till the moisture content is not more than 1.0%

Certain modifications and improvements of the disclosed invention will occur to those skilled in the art without departing from the scope of invention, which is limited only by the appended claims.

We claim:

1. A one pot process for the preparation of candesartan (I) comprises: (a) reacting cyanobiphenyl benzimidazole (III) with trialkyltin or triaryltin azide in presence of an organic solvent to form candesartan ethylester (II); and (b) hydrolyzing the candesartan ethylester (II) in situ and without isolation with an alkali followed by in situ treatment with an acid to yield candesartan (I).

2. The process according to claim 1, wherein the trialkyltin azide or triaryltin azide is trimethyltin azide, tributyltin azide or triphenyltin azide.

3. The process according to claim 2, wherein the trialkyltin azide or triaryltin azide is tributyltin azide.

4. The process according to claim 1, wherein organic solvent is o-xylene, toluene, dimethylformamide, or dimethylacetamide.

5. The process according to claim 4, wherein the organic solvent is o-xylene.

6. The process according to claim 1, wherein the alkali is sodium hydroxide or potassium hydroxide.

7. The process according to claim 6, wherein the alkali is sodium hydroxide.

* * * * *